United States Patent [19]
Bulan et al.

[11] Patent Number: 5,326,437
[45] Date of Patent: Jul. 5, 1994

[54] PROCESS FOR PRODUCTION OF PERFLUOROALKYSULPHONYL FLUORIDES

[76] Inventors: Andreas Bulan; Peter Hafermann; Michael Krancher; Rainer Weber, all of Bayer Aktiengesellschaft, D 5090 Leverkusen, Bayerwerk, Fed. Rep. of Germany

[21] Appl. No.: 26,846

[22] Filed: Mar. 5, 1993

[30] Foreign Application Priority Data

Mar. 16, 1992 [DE] Fed. Rep. of Germany ....... 4208364

[51] Int. Cl.$^5$ ................................................. C25B 3/08
[52] U.S. Cl. .................................. 204/59 F; 204/59 R
[58] Field of Search ............................ 204/59 F, 59 R

[56] References Cited

U.S. PATENT DOCUMENTS

| | | | |
|---|---|---|---|
| 2,519,983 | 8/1950 | Simons | 204/59 F |
| 3,511,761 | 5/1970 | Childs et al. | 204/59 F |
| 3,547,790 | 12/1970 | Dannels et al. | 204/59 F |
| 3,919,057 | 11/1975 | Plattner et al. | 204/59 F |

*Primary Examiner*—John Niebling
*Assistant Examiner*—Edna Wong

[57] ABSTRACT

In the production of perfluoroalkylsulfonyl fluorides by electrolytic fluorination of alkylsulfonyl fluoride, the electrolyte contains anhydrous hydrogen fluoride, an alkylsulfonyl fluoride, and at least one additional component selected from alkaline earth fluorides, alkali tetrafluoroborates, alkali hexafluorophosphates, hexafluorophosphoric acid, tetrafluoroboric acid, boron trioxide, boron trifluoride, or mixtures thereof.

11 Claims, No Drawings

PROCESS FOR PRODUCTION OF PERFLUOROALKYSULPHONYL FLUORIDES

FIELD OF THE INVENTION

The invention relates to a process for production of perfluoroalkylsulphonyl fluorides by electrolytic fluorination in an electrolyte that contains anhydrous hydrogen fluoride and the appropriate alkylsulphonyl fluoride to be fluorinated, at cell voltages of 4 to 6 V.

BACKGROUND AND PRIOR ART

Electrochemical fluorination is a process for production of perfluorinated inorganic and organic compounds that has been known for a long time. Its particular advantage, according to U.S. Pat. No. 2,519,983, is the possibility of fluorinating organic compounds while preserving functional groups, as for example a sulphonyl fluoride group.

Perfluoroalkylsulphonyl fluorides, particularly perfluorooctylsulphonyl fluoride, are used for production of perfluorinated organic compounds that are used for example as active agents in textile and leather finishing, in fire-extinguishing agents and in electroplating technology.

Electrolytic fluorination has been described in a large number of publications. A summary can be found for example in the journal Chem.-Ing.-Tech. 58, 31–38 (1986). Electrofluorination is usually carried out in anhydrous hydrogen fluoride at nickel electrodes with cell voltages of 4 to 6 V. The important disadvantage of the procedures described is that perfluoroalkylsulphonyl fluorides, especially those with more than 5 carbon atoms, can be obtained in fairly prolonged continuous production only in low space-time yield. In this connection the space-time yield specifies how much of the desired product can be produced per unit of time and of anode geometrical area.

To improve the space-time yield it is proposed in U.S. Pat. No. 3,919,057 to carry out the electrolysis at cell voltages of 9 to 15 V. But in continuous, prolonged operation these high cell voltages can lead even after a few days or weeks to falling material yields of the desired perfluoroalkylsulphonyl fluorides. In addition such high cell voltages lead to a large accumulation at the electrodes of sludge caused by by-products as well as, within a short time, to the destruction of the electrodes, so that economic production of perfluoroalkylsulphonyl fluorides, especially those with more than 5 C atoms in the alkyl group, is not possible.

It was therefore the problem of the present invention to make available a process that does not have the aforementioned disadvantages, so that economic production of perfluoroalkylsulphonyl fluorides is possible.

SUMMARY OF THE INVENTION

It has now surprisingly been found that the production of perfluoroalkylsulphonyl fluorides can be carried out by electrolytic fluorination with high space-time yield at low cell voltage if alkaline earth fluorides, alkali tetrafluoroborates, alkali hexafluorophosphates, hexafluorophosphoric acid, tetrafluoroboric acid, boron trioxide or boron trifluoride or mixtures of these compounds are added to the electrolyte.

The subject-matter of the invention relates to a process for production of perfluoroalkylsulphonyl fluorides by electrolytic fluorination at a cell voltage of 4 to 6 V in an electrolyte that contains anhydrous hydrogen fluoride and the appropriate alkylsulphonyl fluoride to be fluorinated, characterized in that alkaline earth fluorides, alkali tetrafluoroborates, alkali hexafluorophosphates, hexafluorophosphoric acid, tetrafluoroboric acid, boron trioxide, boron trifluoride or mixtures of these compounds are added to the electrolyte of anhydrous hydrogen fluoride and the alkylsulphonyl fluoride to be fluorinated.

DESCRIPTION OF THE PREFERRED EMBODIMENTS

Suitable alkaline earth fluorides are e.g. strontium and barium fluoride. Suitable alkali tetrafluoroborates are e.g. lithium, sodium and potassium tetrafluoroborate. Suitable alkali hexafluorophosphates are e.g. sodium or potassium hexafluorophosphate. The additives are preferably present in the electrolyte in an amount of 0.08–2 mole %, based on the quantity of HF.

Alkylsulphonyl fluorides with 4 to 15 carbon atoms, especially with 6 to 10 carbon atoms in the alkyl group are preferably used.

In the execution of the process according to the invention, perfluoroalkylsulphonyl fluorides, especially perfluoroalkylsulphonyl fluorides with more than 5 carbon atoms, are obtained in continuous operation, even over several months, with high space-time yields that are clearly superior to those of the processes without addition of the compounds mentioned.

In addition, as a result of the addition of the compounds mentioned, the specific energy requirement for production of perfluoroalkylsulphonyl fluorides becomes smaller.

The electrolysis cells usually used for electrolytic fluorination consist of nickel or another material resistant to corrosion by hydrogen fluoride, as for example perfluorinated plastics. The anodes consist in general of nickel and the cathodes of nickel or iron. The separations of the electrodes are usually 2 to 5 mm. The electrolyte temperature is usually between 0° C. and 20° C., but, as described in U.S. Pat. No. 3,919,057, it can also be between 20° C. and 50° C. Further details on the construction and operating conditions of the electrolysis cells can be obtained from the above-quoted literature sources.

The process according to the invention can be used generally for the electrolytic fluorination of alkylsulphonyl fluorides.

The process according to the invention can be carried out e.g. by charging hydrogen fluoride and one of the aforementioned additional compounds as well as 2 wt. %, relative to the hydrogen fluoride used, of the alkylsulphonyl fluoride. A constant cell voltage of 4 to 6 V, preferably 5 V, is then applied, and the alkylsulphonyl fluoride continuously metered in subsequently according to the amount of current that has flowed and the given stoichiometry. The perfluoroalkylsulphonyl fluoride is discontinuously removed from the cell at fixed time intervals.

The invention will be explained in more detail with the aid of the following examples.

EXAMPLE 1

Prior Art

Perfluorooctylsulphonyl fluoride ($C_8F_{17}SO_2F$) was produced by electrolytic fluorination of octylsulphonyl fluoride ($C_8H_{17}SO_2F$) in anhydrous hydrogen fluoride. The reaction occurred in an electrolytic cell with a volume of 32 l that was equipped with nickel sheets as electrodes. The anode area was 10,000 cm². After filling the electrolytic cell with anhydrous hydrogen fluoride and octylsulphonyl fluoride, a cell voltage of 5 V was applied, whereby a current density of 4 mÅ/cm² was established. Within 1,001 hours, the current density fell to 1 mÅ/cm².

The electrolyte temperature during the electrolysis was 10° C.

During the experiment, octylsulphonyl fluoride and anhydrous hydrogen fluoride were replenished from time to time in an amount which had been consumed. The product, perfluorooctylsulphonyl fluoride, was removed from the cell and purified with water and subsequent distillation.

During the experiment, at a constant cell voltage of 5 V, the current density and the space-time yield fell away greatly.

During the electrolysis time of 3,083 hours, 3.46 kg $C_8F_{17}SO_2F$ were produced with 100 kWh, corresponding to 28.8 kWh per kg $C_8F_{17}SO_2F$.

The results of the experiment are shown in Table 1.

TABLE 1

| Electrolysis time [h] | Charge flow [Ah/cm²]* | Current density [mA/cm²]* | Space-time yield $10^{-6}$ g $C_8F_{17}SO_2F$ h × cm² |
|---|---|---|---|
| 1 | 0.01 | 4 | — |
| 1001 | 2.0 | 1 | 300.5 |
| 3083 | 4.1 | 1 | 199.3 |

*The "cm²" value refers to the anode area

EXAMPLE 2

According to the Invention

In this experiment 2 wt % sodium tetrafluoroborate, relative to the weight of hydrogen fluoride used, was additionally added to the electrolyte. The other experimental conditions corresponded to those of Example 1. The results show that perfluorooctylsulphonyl fluoride can be produced with high space-time yields by the process according to the invention.

The space-time yields obtained during the experiment were clearly above those in the experiment without addition of sodium tetrafluoroborate.

During the electrolysis time of 3,100 hours, 28.3 kg $C_8F_{17}SO_2F$ were produced with 684.3 kWh, that is 4.83 kWh per kg $C_8F_{17}SO_2F$.

The results are shown in Table 2.

TABLE 2

| Electrolysis time [h] | Charge flow [Ah/cm²]* | Current density [mA/cm²]* | Space-time yield $10^{-6}$ g $C_8F_{17}SO_2F$ h × cm² |
|---|---|---|---|
| 927.5 | 3.31 | 5.0 | 737.2 |
| 1837.5 | 8.11 | 5.5 | 971.5 |
| 2553.5 | 11.90 | 4.9 | 1225.5 |
| 3100 | 14.00 | 3.2 | 666.8 |

*The "cm²" value refers to the anode area

What is claimed is:

1. In a process for the production of perfluoroalkylsulphonyl fluorides by electrolytic fluorination in a liquid mixture of anhydrous HF and alkylsulphonyl fluoride, the improvement which comprises including in the liquid solution at least one electrolyte component selected from the group consisting of alkaline earth fluorides, alkali tetrafluoroborates, alkali hexafluorophosphates, hexafluorophosphoric acid, tetrafluoroboric acid, boron trioxide, boron trifluoride and mixtures thereof.

2. The process as claimed in claim 1, wherein the alkylsulphonyl fluoride has an alkyl group with 4 to 15 carbon atoms.

3. A process as claimed in claim 2, wherein the alkylsulphonyl fluoride has an alkyl group with 6 to 10 carbon atoms.

4. The process as claimed in claim 1, wherein the electrolyte component is present in an amount of 0.08–2 mole %, based on the quantity of HF.

5. The process as claimed in claim 1, wherein the electrolyte component is an alkaline earth fluoride.

6. The process as claimed in claim 1, wherein the electrolyte component is an alkali tetrafluoroborate.

7. The process as claimed in claim 1, wherein the electrolyte component is an alkali hexafluorophosphate.

8. The process as claimed in claim 1, wherein the electrolyte component is hexafluorophosphoric acid.

9. The process as claimed in claim 1, wherein the electrolyte component is tetrafluoroboric acid.

10. The process as claimed in claim 1, wherein the electrolyte component is boron trioxide.

11. The process as claimed in claim 1, wherein the electrolyte component is boron trifluoride.

* * * * *